United States Patent [19]

Son

[11] Patent Number: 5,342,583

[45] Date of Patent: Aug. 30, 1994

[54] PATIENT'S STOOL AND URINE DISPOSING APPARATUS

[76] Inventor: Jong E. Son, Sekyeong 3cha Apt. 301-609, 845-1, Hupyeong 1 Dong, Chuncheon City, Kangwon-Do, Rep. of Korea

[21] Appl. No.: 964,857

[22] Filed: Oct. 22, 1992

[30] Foreign Application Priority Data

Oct. 24, 1991 [KR] Rep. of Korea ............ 18742

[51] Int. Cl.$^5$ ............................................. G05B 7/00
[52] U.S. Cl. ......................................... 422/107; 2/2;
2/84; 4/316; 4/420.2; 4/449; 4/453; 340/573;
600/19; 600/20; 604/393; 422/105; 422/108
[58] Field of Search .................. 422/107, 108, 105;
604/393; 600/20, 19; 2/DIG. 1, 2, 2.1, 2.11,
2.12, 2.13, 2.14, 84; 4/453, 420.2, 449, 316;
340/573

[56] References Cited

U.S. PATENT DOCUMENTS

| | | | |
|---|---|---|---|
| 2,300,109 | 10/1942 | Dahlke | 4/450 X |
| 2,491,799 | 12/1949 | Clarke | 604/393 X |
| 2,749,558 | 6/1956 | Lent et al. | 4/316 |
| 2,826,758 | 3/1958 | Kahn | 2/DIG. 1 X |
| 2,880,727 | 4/1959 | Whalen | 2/DIG. 1 X |
| 3,034,131 | 5/1962 | Lent | 4/316 |
| 3,340,543 | 9/1967 | Cella | 4/449 X |
| 3,340,544 | 9/1967 | Cella | 4/449 X |
| 3,460,123 | 8/1969 | Bass | 340/573 |
| 3,486,173 | 12/1969 | Youngblood et al. | 4/453 X |
| 3,508,234 | 4/1970 | Snyder | 340/573 |
| 3,751,727 | 8/1973 | Shepard et al. | 600/20 X |
| 4,106,001 | 8/1978 | Mahoney | 340/573 |
| 4,146,933 | 4/1979 | Jenkins et al. | 2/DIG. 1 X |
| 4,205,671 | 6/1980 | Lassen | 128/138 A |
| 4,422,189 | 12/1983 | Couvrette | 4/420.2 |
| 4,438,650 | 3/1984 | Meek | 600/20 X |
| 4,583,522 | 4/1986 | Aronne | 600/20 X |
| 4,619,004 | 10/1986 | Won | 2/DIG. 1 |
| 4,653,126 | 3/1987 | Morandi et al. | 4/420.2 |
| 4,653,491 | 3/1987 | Okada et al. | 128/138 A |
| 4,738,260 | 4/1988 | Brown | 128/138 A |
| 4,754,264 | 6/1988 | Okada et al. | 340/573 |
| 4,768,023 | 8/1988 | Xie | 340/573 |
| 4,842,596 | 6/1989 | Kielpikowski et al. | 604/385.2 |
| 5,043,704 | 8/1991 | Blakeney | 340/573 |
| 5,135,522 | 8/1992 | Fahrenkrug et al. | 604/385.1 |

Primary Examiner—James C. Housel
Assistant Examiner—Harold Y. Pyon
Attorney, Agent, or Firm—Jones, Tullar & Cooper

[57] ABSTRACT

An automatic stool and urine disposing apparatus provides disposal even if a patient is unconscious or is disabled, without requiring the help of a care taker. This apparatus is composed of a wearing section, a disposal device installed in an aperture in the wearing section, a washing device incorporated in the disposal device, and a driving section for operating the device. The wearing section includes a disposing device having a fan operated by a motor, a water detecting sensor, a discharge aperture, and washing water and air supply holes. Also attached to the wearing section is an inflatable pressing tube which prevents leakage. The driving section includes relays for operating the disposing device in response to the presence of material to be disposed.

19 Claims, 7 Drawing Sheets

PATIENT'S STOOL AND URINE DISPOSING APPARATUS

FIELD OF THE INVENTION

The present invention relates to a patient's stool and urine disposing apparatus in which stool and urine can be automatically disposed in cases where a patient has lost consciousness, or where a patient who is conscious is so disabled as not to be able to move himself or herself.

BACKGROUND OF THE INVENTION

As is well known, if a hospitalized patient can move around, he or she can use a bath room, and therefore, there arises little or no inconvenience in the patient's personal care. On the other hand, if a patient has lost consciousness, or if a patient cannot walk even if conscious, the patient must excrete waste while lying down, and a care taker has to dispose of the excretion.

Of course, a patient who is conscious can express his or her wish to perform an excretion, and a care taker can furnish a means for disposing of it, and can afterwards clean the relevant body portion of the patient. However, an unconscious patient discharges excretions at any time without calling the care taker's attention, with the result that not only the clothes of the patient but also the patient's bed can become soiled. Care takers experience great difficulties in taking care of such patients.

SUMMARY OF THE INVENTION

The present invention is intended to solve the above described difficulties.

Therefore, it is an object of the present invention to provide a stool and urine disposing apparatus in which the stool and urine excreted by a patient can be immediately and automatically sensed and disposed.

In achieving the above object, a patient's stool and urine disposing apparatus according to the present invention includes: a wearing section which can be put on a patient like an undergarment, such as shorts or panties; a driving section for disposing of the excretions; and an electrical circuit for automatic operation of the driving section.

The apparatus of the present invention is operated in such a manner that if stool or urine, or both, are excreted by a patient, a sensor installed within the wearing section detects the excretion. The electrical circuit then causes the driving section to be driven to inject water into the wearing section and a fan is driven in order to crush the stool. The crushed stool together with the water is then sucked out by means of a hose to clean the interior of the wearing section and then air is blown into the wearing section automatically in order to dry up the interior of the wearing section and the relevant body portion of the patient.

BRIEF DESCRIPTION OF THE DRAWINGS

The foregoing, and additional objects, features and advantages of the present invention will become apparent to those of skill in the art from the following detailed description of a preferred embodiment thereof, taken with the accompanying drawings in which.

DESCRIPTION OF THE PREFERRED EMBODIMENT

Figure 1:
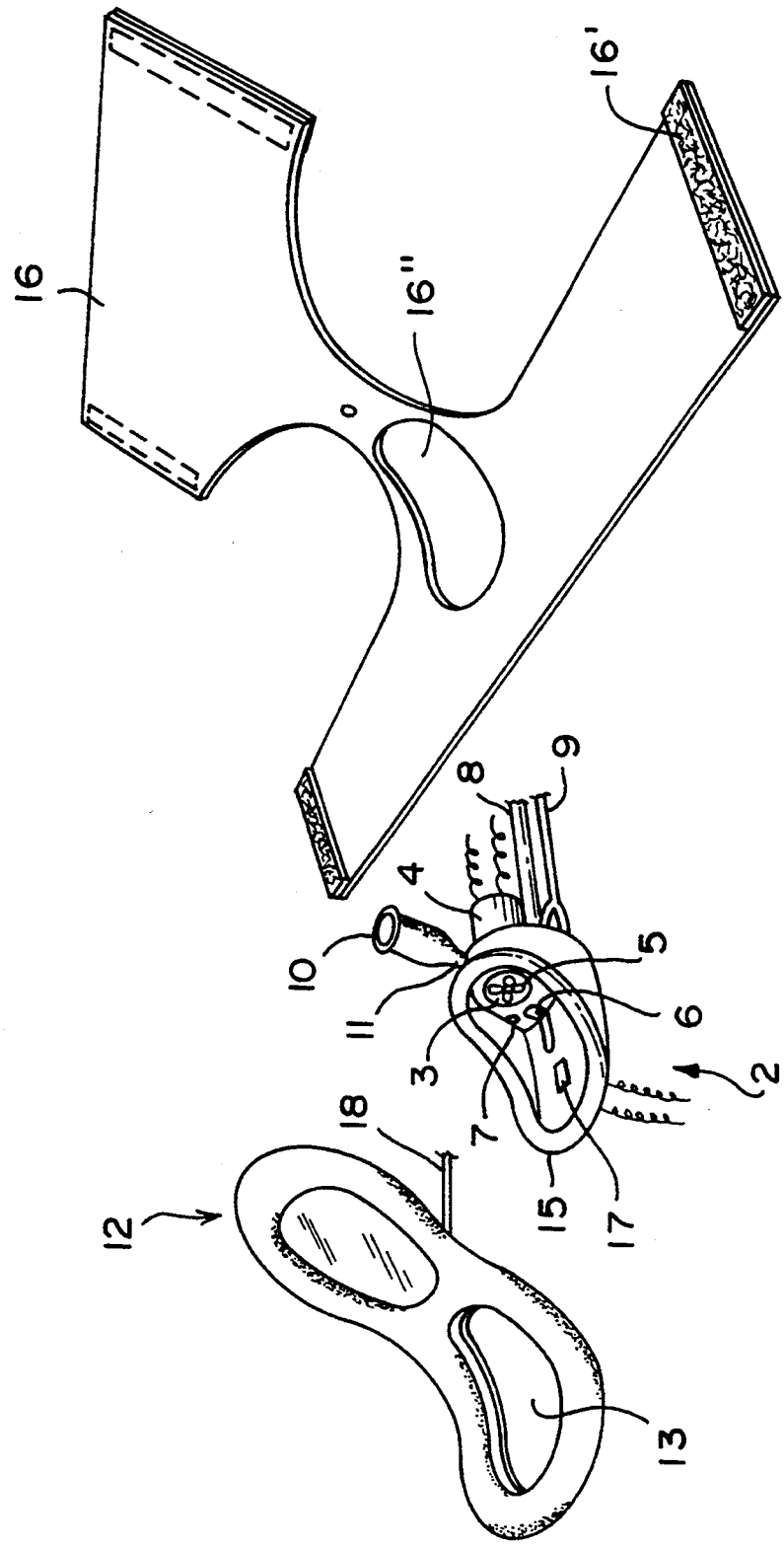
FIG. 1 is an exploded perspective view of the wearing section of the apparatus of the present invention.
Figure 2:
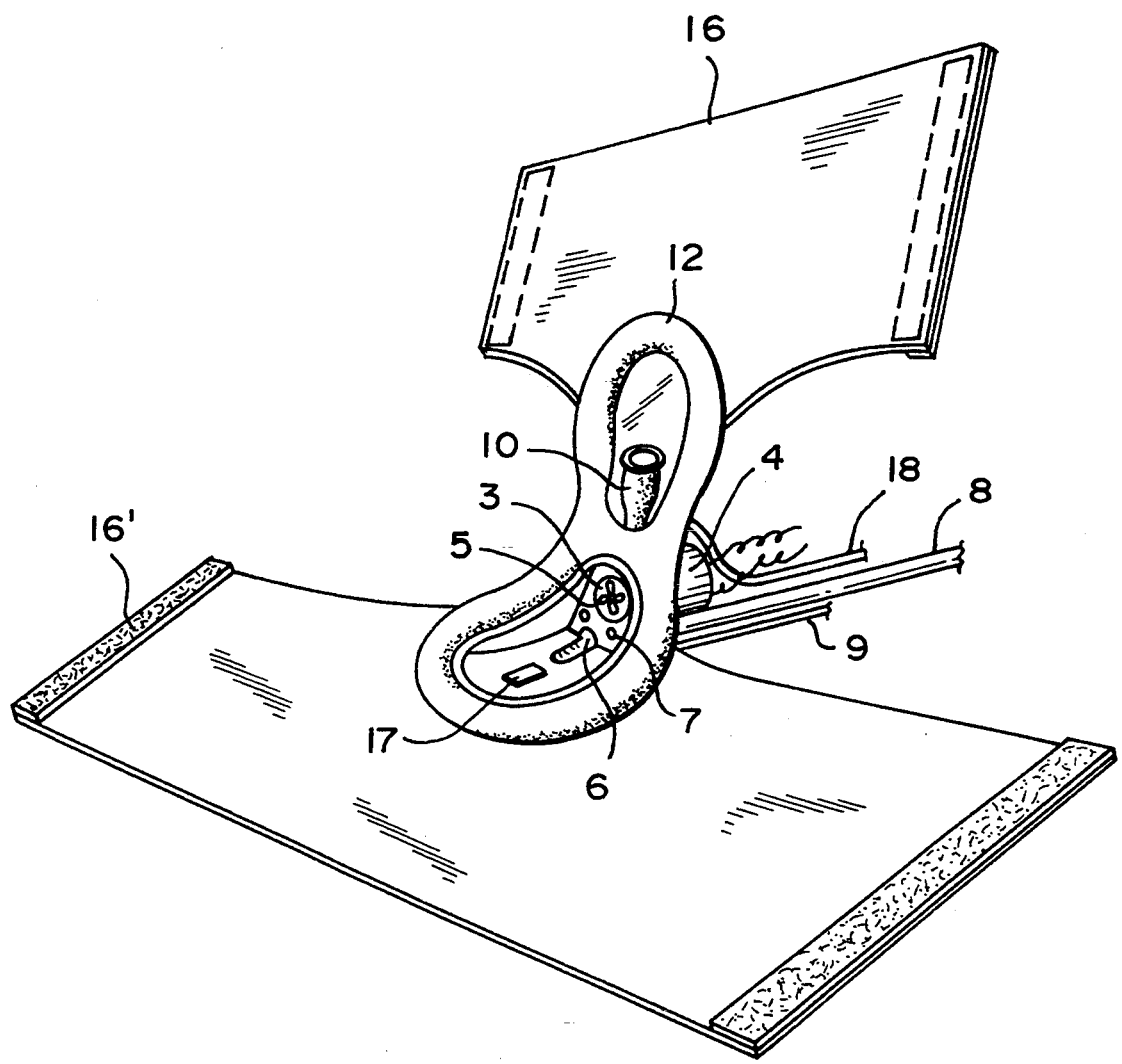
FIG. 2 is a perspective view of the assembled wearing section of FIG. 1.

The preferred embodiment of the present invention will now be described in detail, with reference to the attached drawings wherein a wearing section of the disposing apparatus is illustrated in FIGS. 1, 2, and 3. As there illustrated, the wearing section includes a panty cloth 16 generally in the shape of a diaper of the type used for babies, with attaching strips 16' located along lateral edges thereof, and having an aperture 16" for receiving a disposing device 2 and an inflatable pressing tube 12. The pressing tube 12 is in the shape of a numeral eight, and includes a lower end portion which is large enough to receive the hips of a patient. An aperture 13 is formed in the lower portion of the pressing tube 12, the aperture having a similar shape to the aperture 16". The inflatable pressing tube is attached to one side of panty cloth 16 (the upper side as viewed in FIG. 1) while the disposing device 2 is located on the lower side of cloth 16 and includes an upper peripheral rim 15 which extends through aperture 16" and into aperture 13 to engage the pressing tube 12. As illustrated in FIGS. 3A and 3B, the peripheral rim 15 includes an upwardly and outwardly extending flange which extends through aperture 16" and into aperture 13 to engage a corresponding inwardly extending rim or shoulder in aperture 13 to secure the disposing device 2 to the panty cloth 16.

Figure 3A:
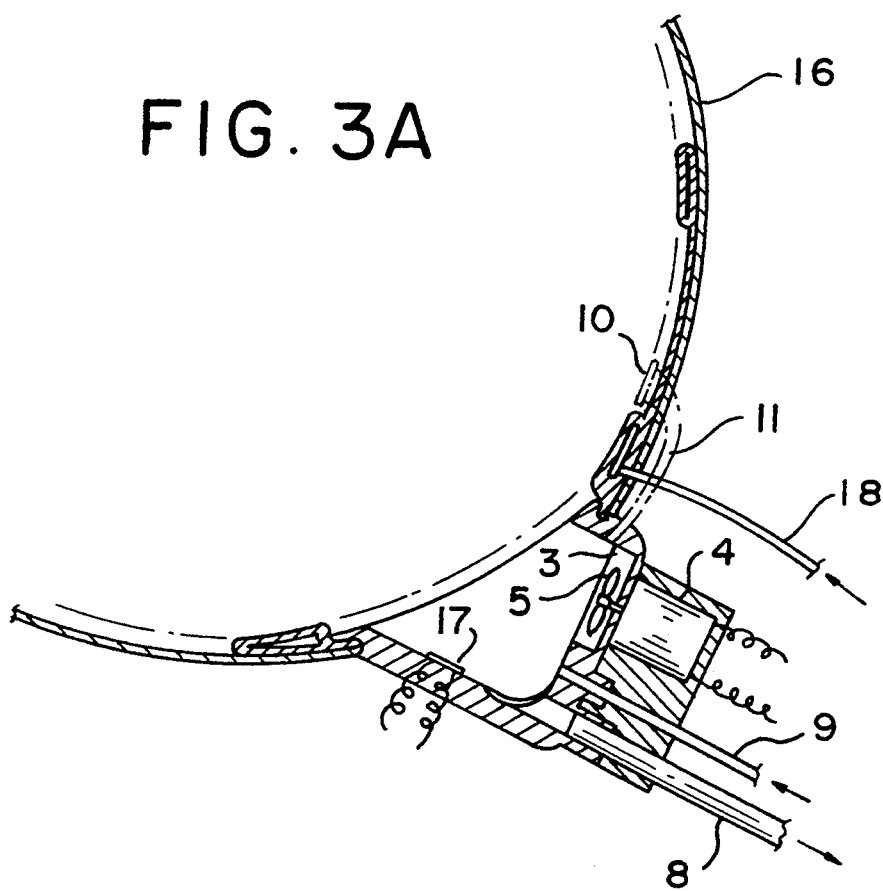
FIG. 3A is a sectional view of a pressing tube, before air is injected.
Figure 3B:
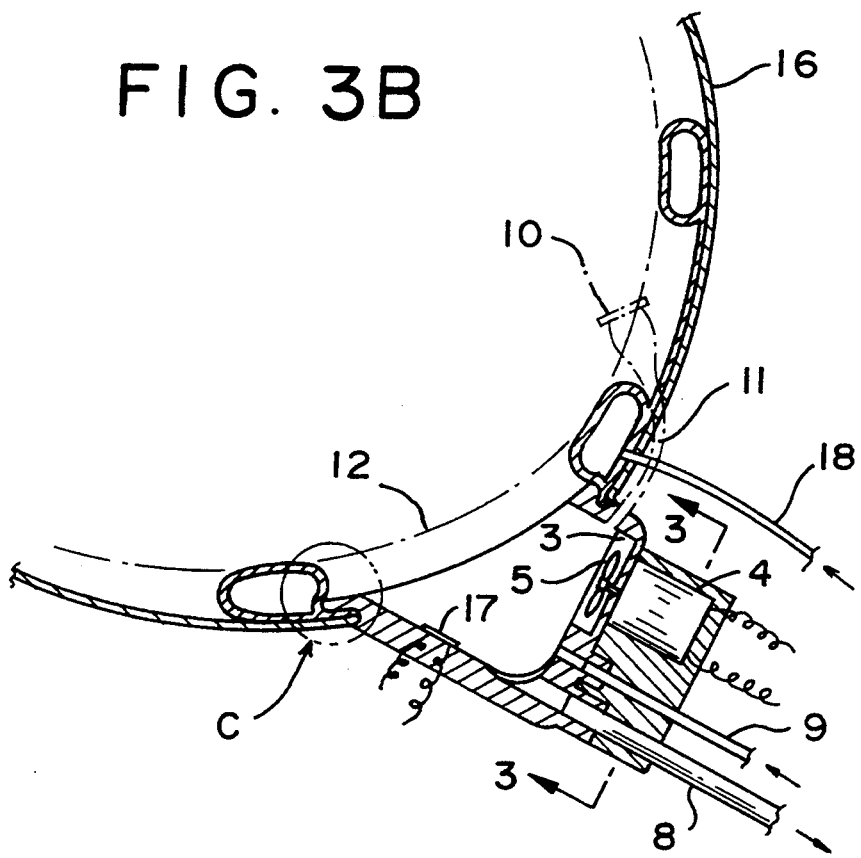
FIG. 3B is a sectional view of the pressing tube, with air being injected therein.
Figure 3C:
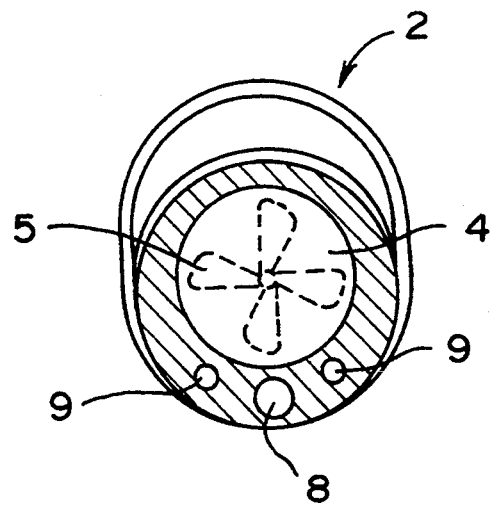
FIG. 3C is a sectional view taken along the line B—B of FIG. 3B.
Figure 3D:
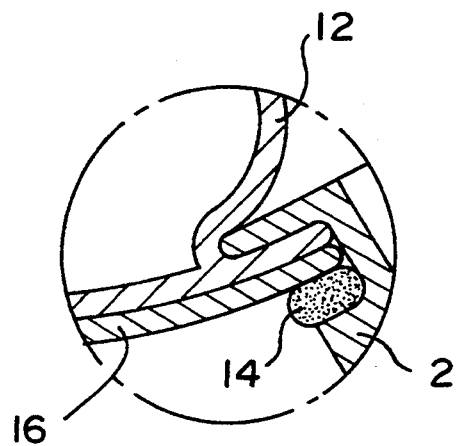
FIG. 3D is an enlarged illustration of the portion C of FIG. 3B.

As best seen in FIGS. 3B and 3D, a packing device such as a silicon rubber ring 14 is installed in a groove formed adjacent to peripheral flange 15 in the disposing device 2. This groove receives the inner periphery of aperture 16" and also receives the inner peripheral shoulder of aperture 13 to secure the disposing device to the panty cloth 16 and to prevent leakage around the edge of the disposing device 2. Inflation of the pressing tube 12 by means of air supply hose 18 also serves to prevent leakage by pressing the upper surface of the tube against a patient and the lower surface of the tube against the surface of disposing device 2.

The disposing device 2 includes a cavity having a bottom wall in which is located an opening 3 which receives a fan 5 driven by a small motor 4, the fan being located in the opening 3 and the motor being outside the wall of the disposing device. Also located on the floor of the disposing device 2 is a discharge hole 6 adjacent the fan opening 3. Water and air supply holes 7 are provided at both sides of the discharge hole 6 and a water and air supply hose 9 is connected thereto in such a manner that water and air can be selectively directed into the cavity and toward the patient when the panty cloth is worn. A water detecting sensor 17 is installed on the front portion of the bottom wall of the disposing device 2, near and in front of the discharge hole 6. A tube 10 for collecting urine is connected by way of a connecting hose 11 to the interior of the disposing device 2, as best illustrated in FIGS. 3A and 3B.

Figure 4:
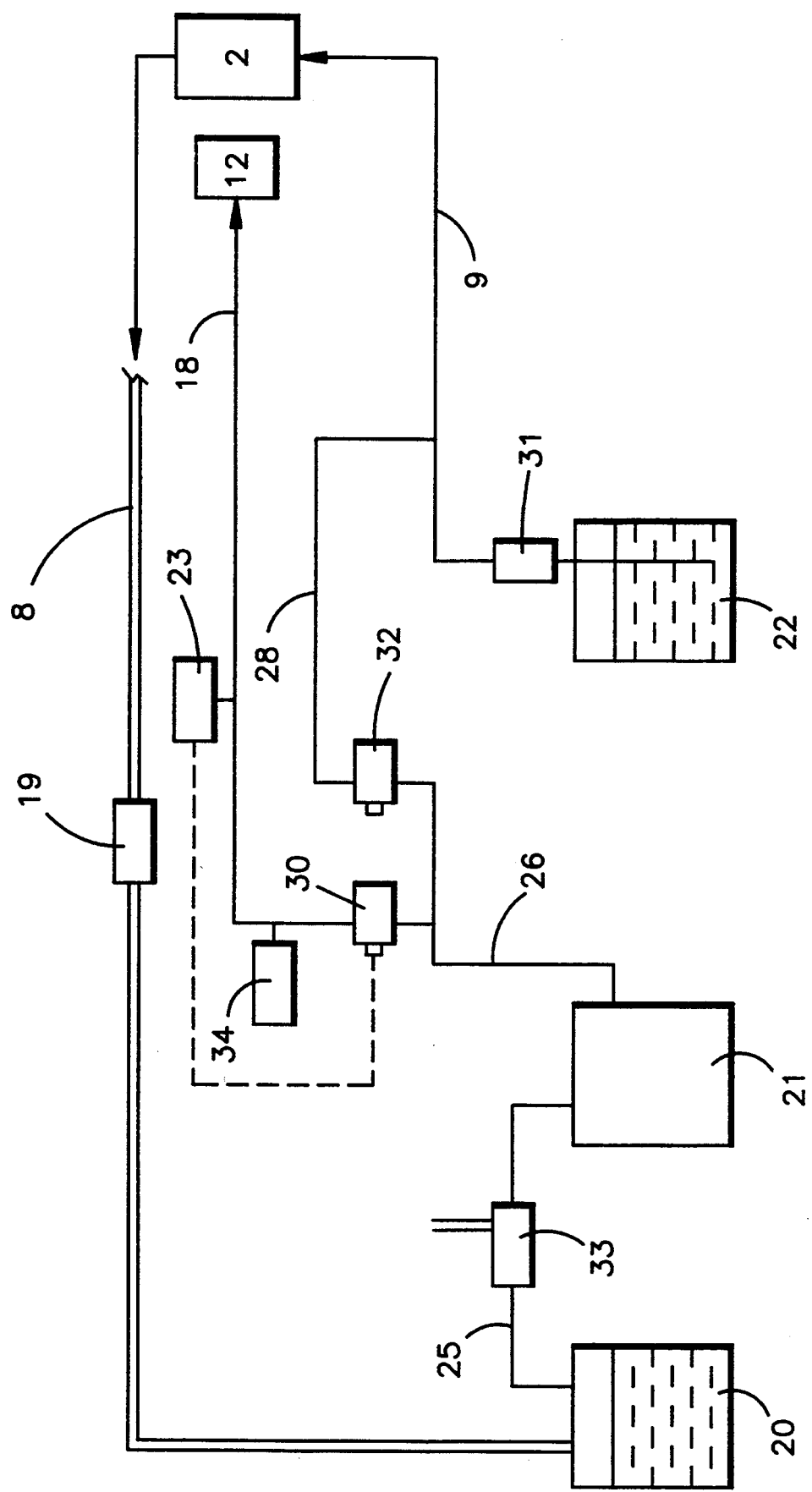
FIG. 4 is a block diagram showing the driving section.

The wearing section described above is connected to a driving section for the present invention, such as that illustrated in FIG. 4. The driving section includes a recovery tank 20 which is connected to the vacuum side of an air compressor 21 and which includes a suction line 8 connected to the discharge hole 6 of the disposing device 2. The driving section further includes a cleaning water supply tank 22 which supplies water by way of a water pump 31 to water supply hose 9 and thus to the water and air supply holes 7. The supply hose 9 is also connected to the pressure side of air compressor 21 by way of pressure line 26 and air supply valve 32 so that the water and air sources are connected in parallel to the disposing device 2 by way of line 9. In addition, air from pressure line 26 is supplied by way of air supply valve 30 and supply hose 18 to the inflatable pressing tube 12 to inflate the tube. In order to control the air supply valve 32, a pressure sensing switch 23 is provided in line 18, whereby the pressure supply to the pressing tube 12 is regulated to control the pressure with which it engages a patient, and thus to control leakage of fluids from the disposing apparatus.

Figure 5:
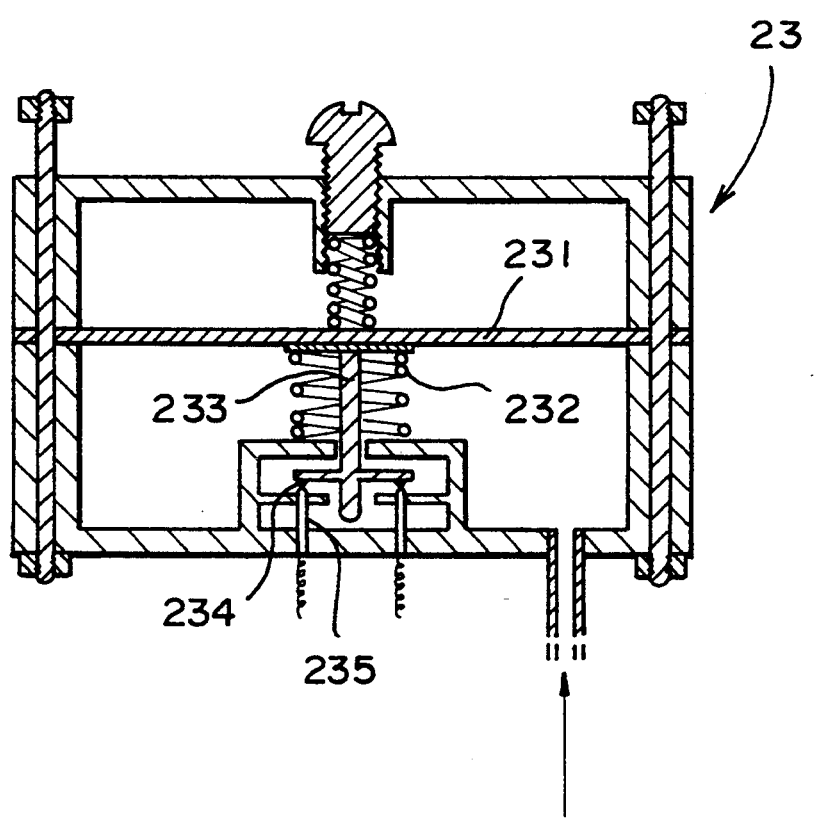
FIG. 5 is a sectional view showing the operating state of the air supply control device.

The pressure sensing switch 23 is illustrated in greater detail in FIG. 5 as including a diaphragm 231 which is by biased by a spring 232. A shaft 233 is connected at its upper end to the diaphragm and carries at its lower end movable contacts 234 which engage stationary contacts 235 when the diaphragm moves downwardly against spring 232. Air under pressure from line 18 enters the lower chamber of diaphragm switch 23 and urges the diaphragm upwardly against an adjustable spring so that the contacts 234 are disconnected from contacts 235 to control valve 30 and to limit the pressure of the air supplied to pressing tube 12.

A discharge valve 34 is connected in line 18 to permit release of the pressure in pressing tube 12 at the conclusion of the discharge cycle.

An external air supply triple valve 33 is connected in line 25 between recovery tank 20 and compressor 21 to permit control of the vacuum in recovery tank 20. A salt detecting sensor 19 for detecting the presence of body fluids from a patient is installed in the discharge hose 8 in order to disable the water pump 31 when no salt is detected in the water being discharged from the disposing device 2.

Figure 6:
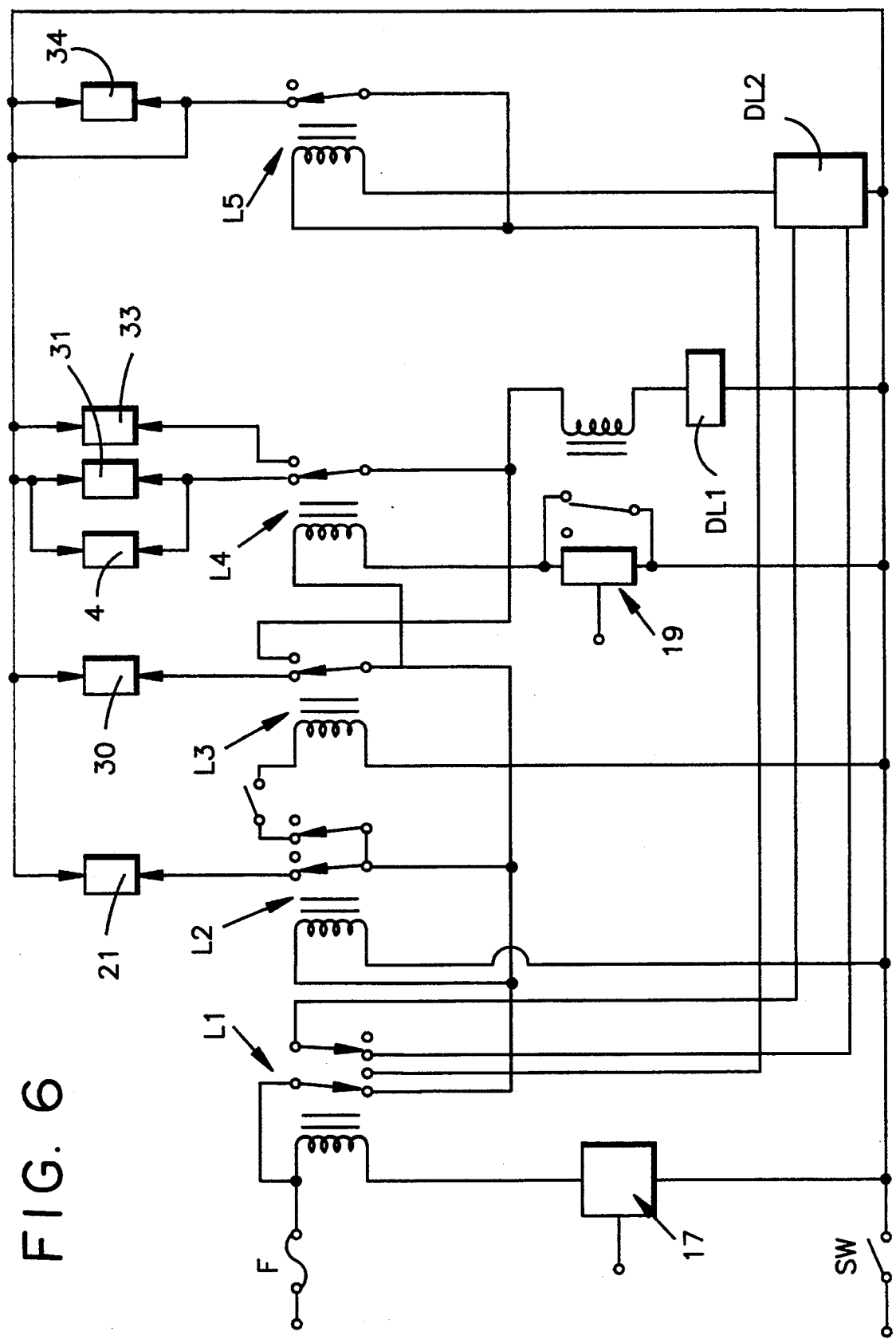
FIG. 6 illustrates the electrical circuit of the apparatus of the present invention.

FIG. 6 illustrates an electrical control circuit for activating the above-described valves and sensors. In this circuit, power from a power supply is connected through a fuse F and a switch SW and through the activating coil of a relay L1 to the water detecting sensor 17. When water is detected, power flows through the coil of relay L1 to activate the movable contacts of the relay and thereby supply power to the entire circuit.

Upon activation of the relay L1, power is supplied to a rely L2 to activate it and to thereby supply driving power to compressor 21. At the same time, a relay L3 is activated to turn on the air supply valve 30 to inflate pressing tube 12. A relay L4 is activated to supply power to motor 4, water pump 31, and the external air supply triple valve 33. Relay L5 is deactivated and its contacts are opened when relay L1 is activated so that the discharge valve 34 is inoperative, thereby allowing the pressing tube 12 to be inflated. However, upon deenergization of relay L1, relay L5 is activated to close its contacts and turn on the discharge valve 34 to deflate the pressing tube 12. Under this latter condition, a delay switch DL2, which is connected in series with relay L5, operates for one minute, and then disconnects power from relay L5, thereby deactivating discharge valve 34 after the pressing tube has deflated.

Relay L4 is initially activated through the normally closed contacts of delay switch DL1 which bypass sensor 19. After four to eight seconds, this delay switch is automatically opens the bypass so that the coil of relay L4 is operated under the control of salt detecting sensor 19 which is connected in series with the relay coil. Sensor 19 turns on upon the detection of salt in the discharge line 8 so that after four to eight seconds, if sensor 19 detects salt, relay L4 remains energized. If no salt is detected; i.e., if the water being discharged is clean, the relay L4 is turned off by sensor 19.

The operation of the stool and urine disposing apparatus of the present invention may be described as follows. First, the panty cloth section 16 of the invention is placed on the patient by first unfolding it and then placing the pressing tube portion 12 below the patient's hip, so as to properly position the disposing device 2 beneath the patient. Then the adhesive portion 16' formed on the edges of the cloth 16 are attached together so as to secure it in place, with the pressing tube surrounding the genitalia of the patient while the pressing tube is in the deflated condition illustrated in FIG. 3A. Power to the driving section of FIG. 6 is then turned on by closing switch SW, placing the circuit in a ready state. The device is not activated, however, until the urine and stool sensor 17, installed on the bottom wall of the disposing device 2 and sensitive to the presence of water, is activated to thereby supply power to relay L1 to turn it on. Power is then simultaneously applied to relays L2, L3, and L4 to turn them on, with the result that the compressor 21 is activated and valve 30 is turned on. Air is then supplied from compressor 21 through the supply hose 26, through valve 30 and through line 18 to inflate the pressing tube 12. The pressure reaction switch 23 limits the pressure of the air supplied to the pressing tube 12 so that there is no possibility of tube 12 bursting, while allowing the pressing tube 12 to be inflated to fill the space between the patients' hips and the apparatus of the present invention. The pressing tube presses against the hips of the patient to prevent leakage and to secure the device in place.

The capacity of the pressing tube 12 is the same as the maximum capacity of the pressure sensing device 23 so that there is no possibility that the pressing tube will burst.

When relay L4 is activated, water pump 31 and motor 4 are turned on. Initially, the salt detecting sensor 19 is off, but the relay L4 is operated by the delay switch DL1, as described above.

When pump 31 is turned on by relay L4, water is supplied through the water and air supply line 9 to holes 7 so that water and/or air is sprayed on the patient for cleaning purposes, and the water is mixed with the excretion. After being mixed with water, the excretion is crushed to a fine grade by the fan 5 of motor 4, and then is withdrawn through discharge hole 6 and discharge hose 8 to the recovery tank 20 by the action of the suction produced in line 25 and tank 20 by compressor 21. When this occurs, salt detecting sensor 19, which is located in discharge hose 8, detects salt and turns on so that even when time relay DL1 times out, the switch 19 will keep the relay L4 in its turned-on state.

The operation continues, so that after termination of excretion by the patient, water is continuously supplied to perform washing operations. When the washing is completed, the salt detecting sensor in discharge hose 8 does will no longer detect any additional salt, and will turn off. Consequently, the electric current which has been supplied to relay L4 is switched off, turning this relay off. The contact arm of relay L4 then switches over, with the result that the motor 4 and the water pump 31 are also turned off and that the air supply valve 32 and the external air supply triple valve 33 are turned on. As a consequence, clean and odorless air is introduced through hose 9 instead of water to dry the patient. This operation is continued until the washed body portions of the patient are dry. When this occurs, sensor 17 turns off and switches off the electric current which has been supplied to relay L1. As a result, relays L1, L2, L3, and L4 are simultaneously turned off while the relay L5 is turned on so that the discharge valve 34 is activated. This allows the internal air in the pressing tube 12 to be discharged backwardly through the air supply hose 18 and out of the system, allowing the pressing tube to return to its original deflated state. This air discharge operation continues for about one minute, and thereafter the electric current to relay L5 is turned off, due to the function of the delay switch DL2, thereby completing the entire operation.

It is noted that the wearing section of the apparatus of the present invention has two different configurations, one for male patients and the other for female patients. The difference between the two types is that the female wearing section has no urine receiving tube 10. It is also understood that although the device is illustrated as being automatically operated, it can also be manually operated. The invention allows easy and convenient care of the patient even if the patient is incapable of standing up.

Although the invention is described in terms of preferred embodiments, it will be understood that variations and modifications may be made without departing from the true spirit and scope thereof as set forth in the following claims.

What is claimed is:

1. A patient's stool and urine disposing apparatus, comprising:
    a panty cloth including fastening means for securing the cloth to a patient and having a disposal aperture;
    sealing means having an aperture corresponding to said disposal aperture;
    a disposing device engaging said cloth disposal aperture and said sealing means aperture to secure said disposing device to said panty cloth and sealing means, said disposing device including:
    a) a cavity connected to said apertures for receiving a patient's stool and urine;
    b) a motor-driven crushing means in said cavity for crushing a patient's stool;
    c) at least one supply hole for directing cleansing water and drying air into said cavity and toward a patient;
    d) a waste outlet for removing crushed stool and urine from said cavity; and
    e) sensor means responsive to water in said cavity for activating said motor-driven crushing means and for supplying water and air to said cavity through said supply hole.

2. The apparatus of claim 1, wherein said sealing means is attached to an inner edge of said disposal aperture of said cloth.

3. The apparatus of claim 2, wherein said sealing means comprises an inflatable tube generally in the shape of the numeral 8, and air supply means connectable to said tube for selectively inflating said tube to seal said disposing apparatus against a patient.

4. The apparatus of claim 3, wherein said air supply means includes a source of air under pressure, an air supply hose connecting said source of air to said tube, and control means regulating the flow of air to said tube.

5. The apparatus of claim 4, wherein said control means includes a control valve connected to said air supply hose and an pressure sensor means regulating said control valve.

6. The apparatus of claim 3, further including air hose means for selectively connecting said air under pressure to said supply hole in said cavity.

7. The apparatus of claim 3, further including water supply means for selectively connecting water under pressure to said supply hole in said cavity.

8. The apparatus of claim 3, further including recovery tank means connected to said waste outlet and means selectively producing a vacuum in said recovery tank for drawing stool and urine from said cavity.

9. The apparatus of claim 8, further including water supply means for selectively connecting water under pressure to said supply hole in said cavity.

10. The apparatus of claim 9, further including air hose means for selectively connecting said air under pressure to said supply hole in said cavity.

11. The apparatus of claim 10, further including electrical control means responsive to said sensor means to energize said motor driven crushing means, activate said air supply means to selectively inflate said tube and selectively supply air to said supply hole in said cavity, activate said water supply means to direct water into said cavity, and activate said means producing a vacuum in said recovery tank.

12. The apparatus of claim 11, said electrical control means further including sensor means connected to said waste outlet for regulating said water supply means.

13. The apparatus of claim 12, said electrical control means further including means for releasing air pressure in said tube.

14. The apparatus of claim 13, wherein said electrical control means includes plural relays responsive to said sensor means responsive to water in said cavity for activating in selected sequence said motor driven crushing means, said air supply means, said water supply means, said vacuum means and said means for releasing air pressure.

15. A patient's stool and urine disposing apparatus, comprising:
    a panty cloth including fastening means for securing the cloth to a patient and having a disposal aperture;
    inflatable tube sealing means attached to an inner edge of said disposal aperture, said inflatable tube having an aperture corresponding to said disposal aperture;

means connectable to said tube for selectively inflating said tube to seal said disposing apparatus against a patient;

a disposing device engaging said cloth disposal aperture and said sealing means aperture to secure said disposing device to said panty cloth and sealing means, said disposing device including:
 a) a cavity connected to said apertures for receiving a patient's stool and urine;
 b) a motor-driven crushing means in said cavity for crushing a patient's stool;
 c) at least one supply hole for directing cleansing water and drying air into said cavity and toward a patient;
 d) a waste outlet for removing crushed stool and urine from said cavity; and,
 e) sensor means responsive to water in said cavity for activating said motor-driven crushing means and for supplying water and air to said cavity through said supply hole;

means selectively applying a vacuum to said waste outlet for drawing stool and urine from said cavity;

water supply means for selectively connecting water under pressure to said supply hole in said cavity;

air supply means for selectively connecting air under pressure to said supply hole in said cavity; and, electrical control means responsive to said sensor means to energize said motor-driven crushing means, activate said air and water supply means to selectively supply air to water to said supply hole in said cavity, and activate said means to apply a vacuum, said electrical control means including sensor means connected to said waste outlet for regulating said water supply means.

16. The apparatus of claim 15, wherein said inflatable tube is generally in the shape of the numeral 8, and wherein said means for selectively inflating includes a source of air under pressure, an air supply hose connecting said source of air to said tube, and control means regulating the flow of air to said tube.

17. The apparatus of claim 16, wherein said control means includes a control valve connected to said air supply hose and a pressure sensor means regulating said control valve.

18. The apparatus of claim 17, wherein said electrical control means further includes means for releasing air pressure in said inflatable tube.

19. The apparatus of claim 18, wherein said electrical control means includes plural relays responsive to said sensor means responsive to water in said cavity for activating in selected sequence said motor-driven crushing means, said air supply means, said water supply means, said vacuum means and said means for releasing air pressure.

* * * * *